US012773286B2

(12) United States Patent
Brisson

(10) Patent No.: US 12,773,286 B2
(45) Date of Patent: *Oct. 27, 2026

(54) REDUCING ENERGY BUILDUP IN SERVO-CONTROLLED MECHANISMS

(71) Applicant: Intuitive Surgical Operations, Inc., Sunnyvale, CA (US)

(72) Inventor: Gabriel Brisson, Livermore, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 18/810,904

(22) Filed: Aug. 21, 2024

(65) Prior Publication Data

US 2024/0407868 A1 Dec. 12, 2024

Related U.S. Application Data

(63) Continuation of application No. 17/598,186, filed as application No. PCT/US2020/025481 on Mar. 27, 2020, now Pat. No. 12,096,998.

(Continued)

(51) Int. Cl.

*A61B 34/30* (2016.01)
*A61B 90/00* (2016.01)
*B25J 9/16* (2006.01)

(52) U.S. Cl.

CPC ............... *A61B 34/30* (2016.02); *B25J 9/163* (2013.01); *B25J 9/1633* (2013.01);

(Continued)

(58) Field of Classification Search

CPC ...... B25J 9/1633; B25J 9/1635; B25J 9/1638; B25J 9/1641; B25J 9/1646; B25J 9/1653;

(Continued)

(56) References Cited

U.S. PATENT DOCUMENTS 5,355,064 A 10/1994 Yoshino et al.
5,691,615 A 11/1997 Kato et al.

(Continued)

FOREIGN PATENT DOCUMENTS

CN 104002856 A 8/2014
EP 2332481 A2 6/2011

(Continued)

OTHER PUBLICATIONS

Extended European Search Report for Application No. EP23187012.2, mailed on Oct. 11, 2023, 08 pages.

(Continued)

*Primary Examiner* — Spencer D Patton

(74) *Attorney, Agent, or Firm* — Osha Bergman Watanabe & Burton LLP

(57) ABSTRACT

A computer-assisted medical system includes a manipulator arm and a controller. The controller includes a computer processor. The controller is configured to servo at least one joint associated with at least one manipulator arm segment of the manipulator arm, the servoing including executing a servo loop. Executing the servo loop includes obtaining an actual state of the manipulator arm, computing a difference between a commanded state and the actual state, where the commanded state is used for the servoing the at least one joint, and determining whether the difference exceeds an error threshold. Based on determining that the difference does exceed the error threshold, the commanded state is updated using an offset to reduce the difference, and. Based on determining that the difference does not exceed the error threshold, the commanded state is not updated. The controller is further configured to apply the commanded state to control the actual state.

18 Claims, 10 Drawing Sheets

Related U.S. Application Data

(60) Provisional application No. 62/826,780, filed on Mar. 29, 2019.

(52) U.S. Cl.
CPC .................. *A61B 2090/066* (2016.02); *G05B 2219/39445* (2013.01); *G05B 2219/45118* (2013.01)

(58) Field of Classification Search
CPC ...... B25J 9/1664; B25J 9/1628; B25J 9/1656; B25J 9/1674; B25J 9/163; A61B 34/30; A61B 2090/066; G05B 2219/36445; G05B 2219/39176; G05B 2219/39183; G05B 2219/39186; G05B 2219/39188; G05B 2219/39206; G05B 2219/39209; G05B 2219/39214; G05B 2219/39321; G05B 2219/39322; G05B 2219/39323; G05B 2219/39325; G05B 2219/39326; G05B 2219/39327; G05B 2219/39329; G05B 2219/39331; G05B 2219/39332; G05B 2219/39333; G05B 2219/39337; G05B 2219/39196; G05B 2219/39445; G05B 2219/41119
See application file for complete search history.

(56) References Cited

U.S. PATENT DOCUMENTS

| | | | | |
|---|---|---|---|---|
| 7,087,049 | B2 | 8/2006 | Nowlin et al. | |
| 8,004,229 | B2 | 8/2011 | Nowlin et al. | |
| 8,541,970 | B2 | 9/2013 | Nowlin et al. | |
| 8,624,537 | B2 | 1/2014 | Nowlin et al. | |
| 8,749,189 | B2 | 6/2014 | Nowlin et al. | |
| 8,749,190 | B2 | 6/2014 | Nowlin et al. | |
| 8,786,241 | B2 | 7/2014 | Nowlin et al. | |
| 8,816,628 | B2 | 8/2014 | Nowlin et al. | |
| 8,823,308 | B2 | 9/2014 | Nowlin et al. | |
| 9,259,281 | B2 | 2/2016 | Griffiths et al. | |
| 9,415,510 | B2 | 8/2016 | Hourtash et al. | |
| 9,452,020 | B2 | 9/2016 | Griffiths et al. | |
| 9,694,495 | B1 | 7/2017 | Edsinger et al. | |
| 10,285,764 | B2 | 5/2019 | Griffiths et al. | |
| 12,096,998 | B2 * | 9/2024 | Brisson | B25J 9/1633 |
| 2007/0138992 | A1 | 6/2007 | Prisco et al. | |
| 2007/0151389 | A1 | 7/2007 | Prisco et al. | |
| 2011/0040404 | A1 | 2/2011 | Diolaiti et al. | |
| 2013/0325254 | A1 | 12/2013 | Goupil et al. | |
| 2015/0032126 | A1 | 1/2015 | Nowlin et al. | |
| 2015/0051733 | A1 | 2/2015 | Nowlin et al. | |
| 2017/0220007 | A1 | 8/2017 | Lopiccolo et al. | |
| 2017/0252116 | A1 | 9/2017 | Ogawa et al. | |
| 2018/0042687 | A1 | 2/2018 | Nowlin et al. | |
| 2018/0168749 | A1 | 6/2018 | Dozeman | |
| 2019/0030716 | A1 * | 1/2019 | Chevallereau | B25J 9/1674 |
| 2020/0189125 | A1 * | 6/2020 | Yamagishi | B25J 9/0006 |
| 2022/0175472 | A1 | 6/2022 | Brisson | |

FOREIGN PATENT DOCUMENTS

| | | | |
|---|---|---|---|
| WO | WO-2006124390 | A2 | 11/2006 |
| WO | WO-2014028699 | A1 | 2/2014 |
| WO | WO-2014028702 | A1 | 2/2014 |
| WO | WO-2014146107 | A1 | 9/2014 |
| WO | WO-2015127078 | A1 | 8/2015 |
| WO | WO-2015142943 | A1 | 9/2015 |

OTHER PUBLICATIONS

International Search Report and Written Opinion for Application No. PCT/US2020/025481 mailed Jul. 13, 2020, 13 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

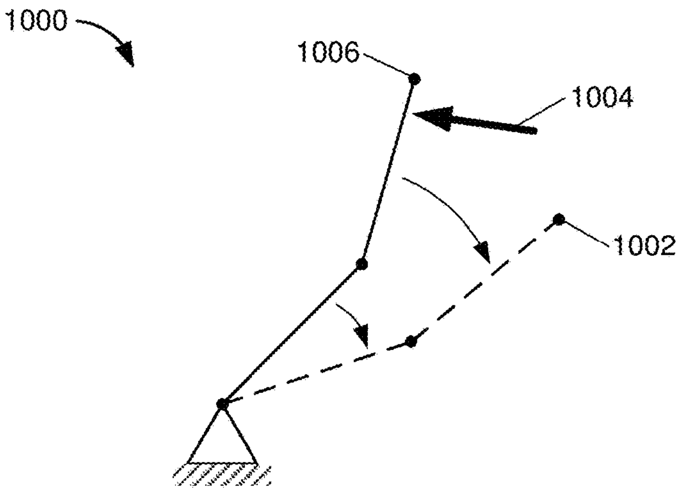
FIG. 10A
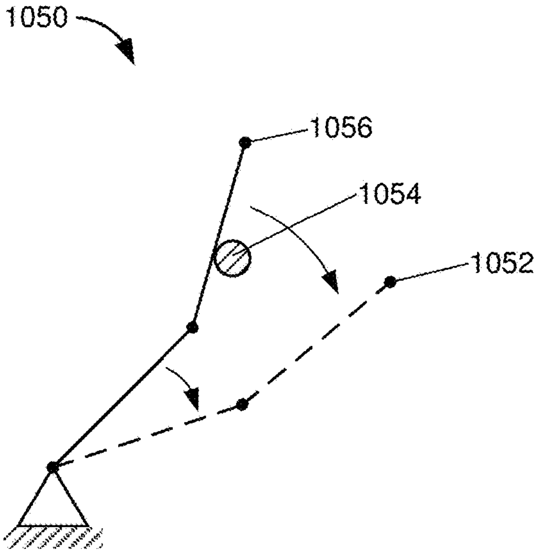
FIG. 10B1
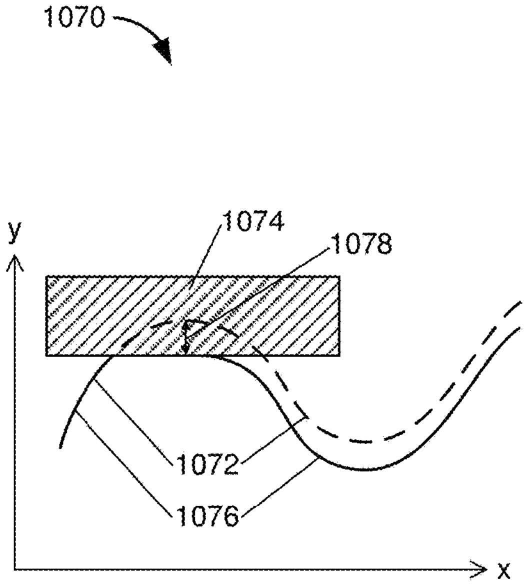
FIG. 10B2

REDUCING ENERGY BUILDUP IN SERVO-CONTROLLED MECHANISMS

CROSS-REFERENCE TO RELATED APPLICATIONS

This application is a continuation of and claims the benefit of priority under 35 U.S.C. § 120 to U.S. patent application Ser. No. 17/598,186, filed on Sep. 24, 2021. U.S. patent application Ser. No. 17/598,186 is a U.S. National Stage Entry of International Application No. PCT/US20/25481, filed on Mar. 27, 2020. International Application No. PCT/US20/25481 claims the benefit of priority under 35 U.S.C. § 119(e) to U.S. Provisional Patent Application Ser. No. 62/826,780, filed on Mar. 29, 2019. All mentioned U.S. patent applications, U.S. provisional patent applications, and international applications are incorporated by reference herein in their entirety.

BACKGROUND

Field of Invention

The present invention generally provides improved robotic and/or medical (including surgical) devices, systems, and methods.

Overview

A system of robotic devices may be used to perform a task at a worksite. For example, robotic systems may include robotic manipulators to manipulate instruments for performing the task. The robotic manipulator may include two or more links coupled together by one or more joints. The joints may be active joints that are actively moved and controlled. The joints may also be passive joints that comply with movement of the active joints or with external manipulation. Such active and passive joints may be revolute or prismatic joints. The configuration of the robotic manipulator may then be determined by the positions and orientations of the joints, the structure of the robotic manipulator, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures may include a remotely controllable robotic manipulator. Operators may remotely control motion of the remotely controllable robotic manipulator. Operators may also manually move pieces of the robotic medical system into positions or orientations within its environment.

SUMMARY

In general, in one aspect, one or more embodiments relate to a computer-assisted medical system comprising a manipulator arm and a controller comprising a computer processor, the controller configured with at least a non-clutch mode. When in the non-clutch mode, the controller is configured to servo at least one joint associated with at least one manipulator arm segment of the manipulator arm, the servoing comprising executing a servo loop comprising: obtaining an actual state of the manipulator arm, computing a difference between a commanded state and the actual state, the commanded state used for the servoing the at least one joint, determining whether the difference exceeds an error threshold, based on determining that the difference does exceed the error threshold: updating the commanded state using an offset to reduce the difference, and applying the commanded state to control the actual state, and based on determining that the difference does not exceed the error threshold: not updating the commanded state, and applying the commanded state to control the actual state.

In general, in one aspect, one or more embodiments relate to a method for operating a medical system. The method comprises, when in a non-clutch mode, servoing at least one joint associated with at least one manipulator arm segment of a manipulator arm of the medical system, the servoing comprising executing a servo loop comprising: obtaining an actual state of the manipulator arm; computing a difference between a commanded state and the actual state, the commanded state used for servoing the at least one joint; determining whether the difference exceeds an error threshold; based on determining that the difference does exceed the error threshold: updating the commanded state using an offset to reduce the difference, and applying the commanded state to control the actual state; and based on determining that the difference does not exceed the error threshold: not updating the commanded state, and applying the commanded state to control the actual state.

In general, in one aspect, one or more embodiments relate to non-transitory machine-readable medium comprising a plurality of machine-readable instructions executed by one or more processors associated with a medical system, the plurality of machine-readable instructions causing the one or more processors to perform a method comprising: in a non-clutch mode, servoing at least one joint associated with at least one manipulator arm segment of a manipulator arm of the medical system, the servoing comprising executing a servo loop comprising: obtaining an actual state of the manipulator arm; computing a difference between a commanded state and the actual state, the commanded state used for the servoing the at least one joint; determining whether the difference exceeds an error threshold; based on determining that the difference does exceed the error threshold: updating the commanded state using an offset that reduces the difference; and applying the commanded state to control the actual state; based on determining that the difference does not exceed the error threshold: not updating the commanded state, and applying the commanded state to control the actual state.

Other aspects of the invention will be apparent from the following description and the appended claims.

BRIEF DESCRIPTION OF DRAWINGS

FIG. 10A schematically shows a manipulator assembly in a position holding task, in accordance with one or more embodiments.

FIGS. 10B1 and 10B2 schematically show a manipulator assembly in a teleoperation task, in accordance with one or more embodiments.

DETAILED DESCRIPTION

Figure 1A:
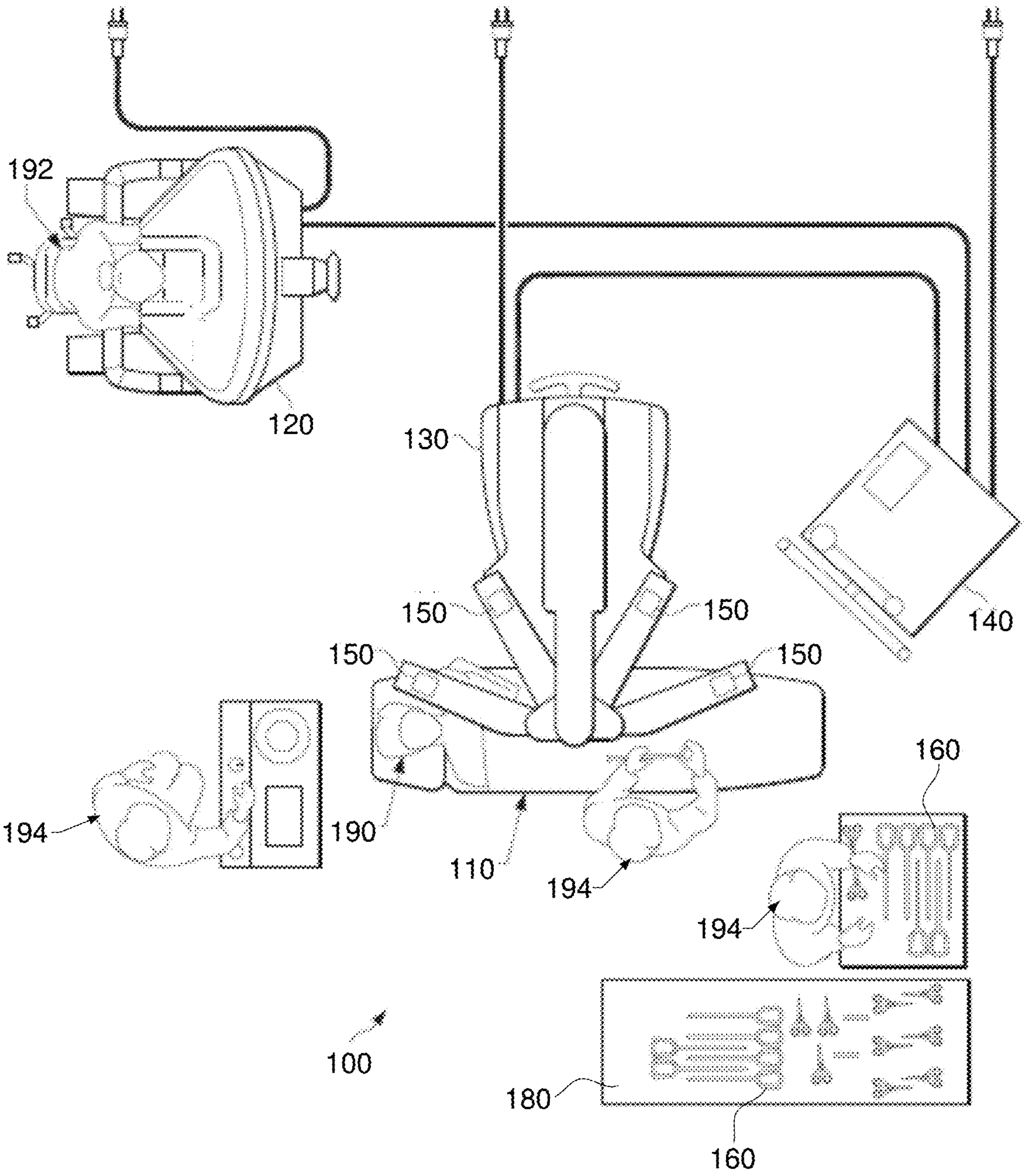
FIG. 1A shows an overhead view of a robotic procedure scenario in accordance with one or more embodiments, the robotic procedure scenario including a robotic assembly using robotic manipulators for robotically moving tools or instruments with end effectors at a worksite.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms “before”, “after”, “single”, and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques may also be used for medical treatment or diagnosis procedures that do, or do not, include surgical aspects.

In general, embodiments of the disclosure may facilitate the use of the robotic systems and improve the workflow under various conditions. For example, a manipulator arm of the robotic system may not always be able to immediately follow a command to reach a commanded position, velocity, or generally speaking a commanded state. Various causes may prevent the manipulator arm from following the command. The result may be a discrepancy between the commanded state and the actual state. This discrepancy may be undesirable for various reasons. For example, when the discrepancy between the commanded state and the actual state is significant, the manipulator arm may perform an abrupt and large amplitude movement, once no longer prevented from moving. Further, while an actual state of the manipulator arm may be directly observable, the commanded state is typically not observable by an operator or assistant. Accordingly, the buildup of the discrepancy may go unnoticed, thus potentially startling the assistant when the movement of the manipulator arm toward the commanded state eventually occurs. The movement may further cause a forceful collision of the manipulator arm with the assistant, the patient, or another component of the robotic system.

Embodiments of the disclosure provide the ability to limit a discrepancy between the commanded state and the actual state of the manipulator arm to an acceptable level. The limiting of the discrepancy, in accordance with one or more embodiments, is applicable to different scenarios including, but not limited to, scenarios in which the manipulator arm is blocked (e.g., by an obstacle), scenarios in which the manipulator arm is externally back-driven, scenarios in which a teleoperation task (i.e., a “following” task where the manipulator arm moves in accordance with commands issued by an operator manipulating an input device that is not the manipulator arm) cannot be completed, etc. Each of these scenarios is described below.

Referring now to the drawings, in which like reference numerals represent like parts throughout the several views, FIG. 1A shows an overhead view of a computer-assisted medical system (100) (hereinafter system (100)) in a robotic procedure scenario. While in FIG. 1A, a minimally invasive robotic surgical system is shown as the computer-assisted medical system (100), the following description is applicable to other scenarios and systems, e.g., non-surgical scenarios or systems, non-medical scenarios or systems. In the example, a diagnostic or surgical procedure is performed on a patient (190) who is lying down on an operating table (110). The system may include a user control system (120) for use by an operator (192) (e.g. a clinician such as surgeon) during the procedure. One or more assistants (194) may also participate in the procedure. The system (100) may further include a robotic manipulating system (130) (e.g., a patient-side robotic device) and an auxiliary system (140). The robotic manipulating system (130) may include at least one manipulator arm (150), each of which may support a removably coupled tool (160) (also called instrument (160)). In the illustrated procedure, the tool (160) may enter the body of the patient (190) through a natural orifice such as the throat or anus, or through an incision, while the operator (192) views the worksite (e.g. a surgical site in the surgical scenario) through the user control system (120). An image of the worksite may be obtained by an imaging device (e.g. an endoscope, an optical camera, or an ultrasonic probe), i.e., a tool (160) used for imaging the worksite, which may be manipulated by the robotic manipulating system (130) so as to position and orient the imaging device. The auxiliary system (140) may be used to process the images of the worksite for display to the operator (192) through the user control system (120) or other display systems located locally or remotely from the procedure. The number of tools (160) used at one time generally depends on the task and space constraints, among other factors. If it is appropriate to change, clean, inspect, or reload one or more of the tools (160) being used during a procedure, an assistant (194) may remove the tool (160) from the manipulator arm (150), and replace it with the same tool (160) or another tool (160), e.g., from a tray (180) or another type of tool storage.

Figure 1B:
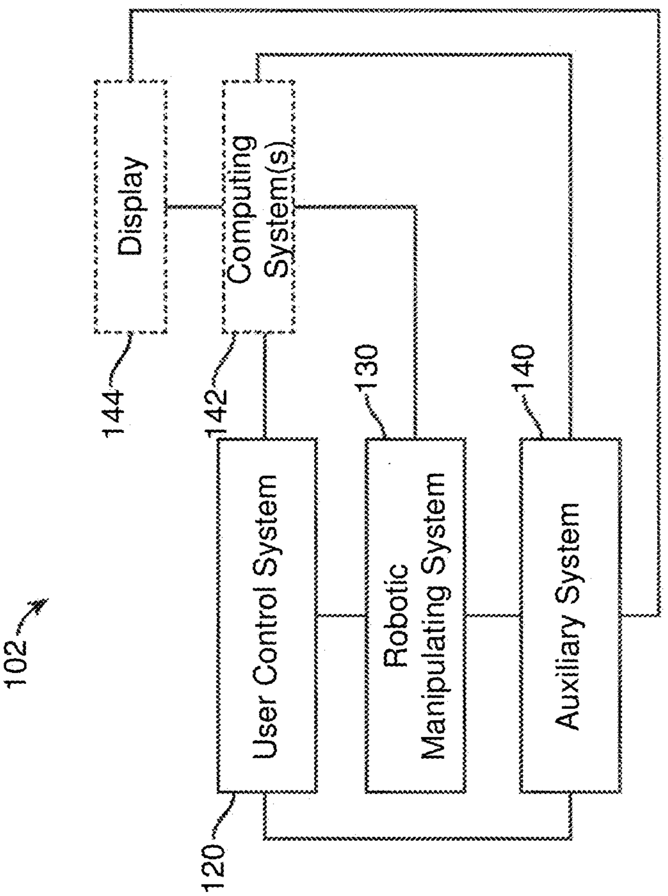
FIG. 1B diagrammatically shows various components of the robotic procedure scenario of FIG. 1A, in accordance with one or more embodiments.

FIG. 1B diagrammatically shows a system (102). The system (102) may include one or more computing systems (142). A computing system (142) may be used to process input provided by the user control system (120) from an operator. A computing system may further be used to provide an output, e.g., a video image to the display (144). One or more computing systems (142) may further be used to control the robotic manipulating system (130).

A computing system (142) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (142) may be an integrated circuit for processing instructions. For example, the computer processor may be one or more cores or micro-cores of a processor. The computing system (142) may also include one or more input devices, such as a touchscreen, keyboard, mouse, microphone, touchpad, electronic pen, or any other type of input device.

A communication interface of a computing system (142) may include an integrated circuit for connecting the computing system (142) to a network (not shown) (e.g., a local area network (LAN), a wide area network (WAN) such as the Internet, mobile network, or any other type of network) and/or to another device, such as another computing system (142).

Further, the computing system (142) may include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

A computing system (142) may be connected to or be a part of a network. The network may include multiple nodes. Each node may correspond to a computing system (142), or a group of nodes. By way of an example, embodiments of the disclosure may be implemented on a node of a distributed system that is connected to other nodes. By way of another example, embodiments of the invention may be implemented on a distributed computing system having multiple nodes, where each portion of the disclosure may be located on a different node within the distributed computing system. Further, one or more elements of the aforementioned computing system (142) may be located at a remote location and connected to the other elements over a network.

The robotic manipulating system (130) may use a tool (160) comprising an imaging device, (e.g., a monoscopic or stereoscopic endoscope, an ultrasonic probe) to capture images of the worksite and output the captured images to an auxiliary system (140). Similar to other tools (160), a tool with an imaging device has a mechanical interface (not shown) allowing the imaging device to be coupled to the manipulator arm (150). The mechanical interface of different tools (160), such as the tool with the imaging device, may be the same or differ from each other. Accordingly, a mechanical adapter may be used where applicable to couple a tool (160) to the manipulator arm (150). Alternatively, a particular tool (160), such as a specialized imaging tool, may be mounted on a manipulator arm (150) specifically designed to accommodate such tools (160). The auxiliary system (140) may process the captured images in a variety of ways prior to any subsequent display. For example, the auxiliary system (140) may overlay the captured images with a virtual control interface prior to displaying the combined images to the operator via the user control system (120). The robotic manipulating system (130) may output the captured images for processing outside the auxiliary system (140). One or more separate displays (144) may also be coupled with a computing system (142) and/or the auxiliary system (140) for local and/or remote display of images, such as images of the procedure site, or other related images.

Figure 2:
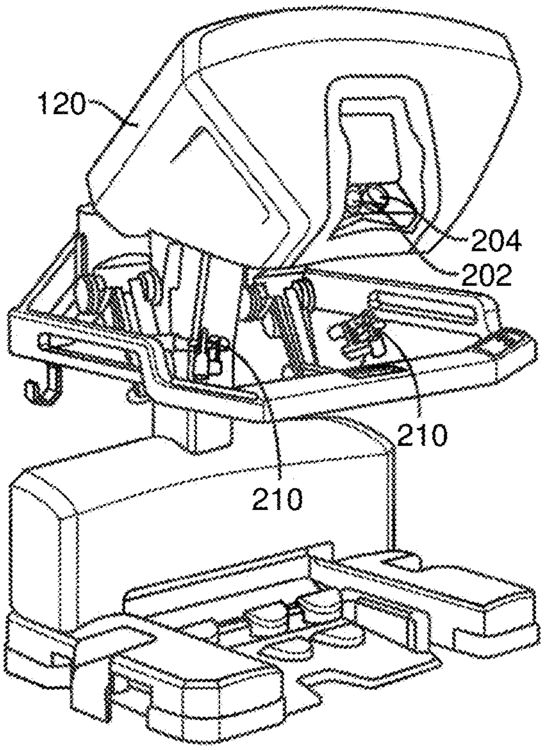
FIG. 2 shows a perspective view illustrating a master operator console or workstation for inputting procedure commands in the robotic assembly of FIG. 1A, in accordance with one or more embodiments.

FIG. 2 shows a perspective view of the user control system (120). The user control system (120) includes a left eye display (202) and a right eye display (204) for presenting the operator (192) (shown in FIG. 1A) with a coordinated stereo view of the worksite that enables depth perception. The user control system (120) further includes one or more input control devices (210), which in turn causes the robotic manipulating system (130) (shown in FIG. 1A) to manipulate one or more tools. The input control devices (210) may provide the same degrees of freedom as their associated tools (160) (shown in FIG. 1A) so as to provide the operator with telepresence, or the perception that the input control devices (210) are integral with the tools (160) (shown in FIG. 1A) so that the operator has a strong sense of directly controlling the tools (160). To this end, position, force, and/or tactile feedback sensors (not shown) may be employed to transmit position, force, and/or tactile sensations from the tools (160) back to the operator's hands through the input control devices (210).

Figure 3:
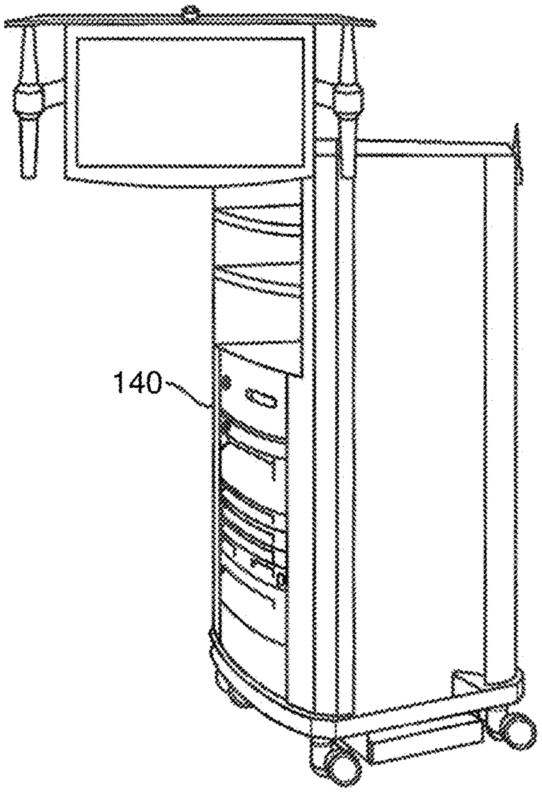
FIG. 3 shows a perspective view of the electronics cart of FIG. 1A, in accordance with one or more embodiments.

FIG. 3 shows a perspective view of the auxiliary system (140). The auxiliary system (140) may be coupled with the imaging device-type tool (160) (shown in FIG. 1A) and may include a processor (not shown) to process captured images for subsequent display, such as to an operator on the operator's console or on another suitable display located locally and/or remotely. For example, where a stereoscopic endoscope is used, the auxiliary system (140) may process the captured images so as to present the operator with coordinated stereo images of the worksite. Such coordination may include alignment between the opposing images and may include adjusting the stereo working distance of the stereoscopic endoscope. As another example, image processing may include the use of previously determined camera calibration parameters so as to compensate for imaging errors of the image capture device, such as optical aberrations.

Figure 4:
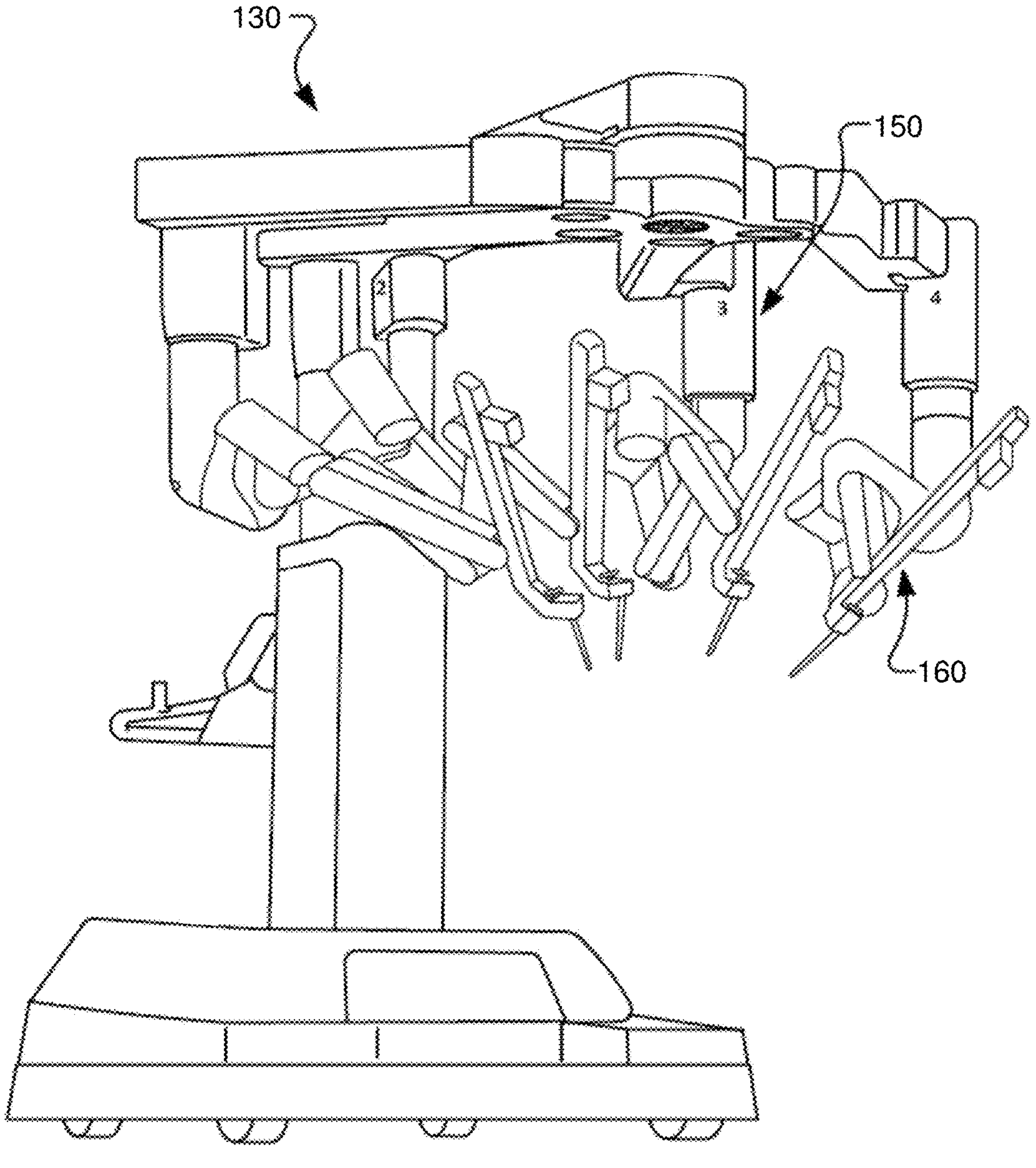
FIG. 4 shows a perspective view of a robotic assembly having four manipulator arms, in accordance with one or more embodiments.

FIG. 4 shows a robotic manipulating system (130) having a plurality of manipulator arms (150), each supporting an instrument or tool (160) at a distal end of the manipulator arm. The robotic manipulating system (130) as shown includes four manipulator arms (150), which may be used to support either a tool (160) for manipulation or tool (160) for imaging, such as a stereoscopic endoscope used for the capture of images of the site of the procedure. A more detailed description of a manipulator arm (150) is provided below with reference to FIG. 5, and a more detailed description of a tool (160) is provided below with reference to FIG. 6. In minimally invasive scenarios, the tools (160) may be positioned and manipulated through incisions in the patient so that a kinematic remote center is maintained at the incision so as to minimize the size of the incision or forces applied to tissue surrounding the incision. Images of the worksite may include images of the distal ends of the instruments or tools (160) when the tools (160) are positioned within the field-of-view of a tool operating as an imaging device.

A variety of tools (160) or instruments of different types and differing end effectors may be used. At least some of the tools (160) may be removed and replaced during a procedure. In surgical scenarios, the end effectors may include, but are not limited to, DeBakey forceps, microforceps, Potts scissors, clip appliers, scalpels and electrocautery probes. Some of these end effectors may have a single end effector element, while other end effectors may include multiple end effector elements, such as first and second end effector elements which may pivot relative to each other so as to define a pair of end effector jaws.

In surgical scenarios, an elongate shaft of a tool (160) allows the end effectors and the distal end of the shaft to be inserted distally into a surgical worksite through a minimally invasive aperture, often through a body wall such as an abdominal wall. The surgical worksite may be insufflated. Movement of the end effectors within the patient is often effected, at least in part, by pivoting of the tool (160) about the location at which the shaft passes through the minimally invasive aperture. Accordingly, manipulator arms (150) may move the proximal housing of the instrument outside the patient so that the shaft extends through a minimally invasive aperture to provide a desired movement of end effector. Hence, manipulator arms (150) may undergo movement outside the patient.

Figure 5:
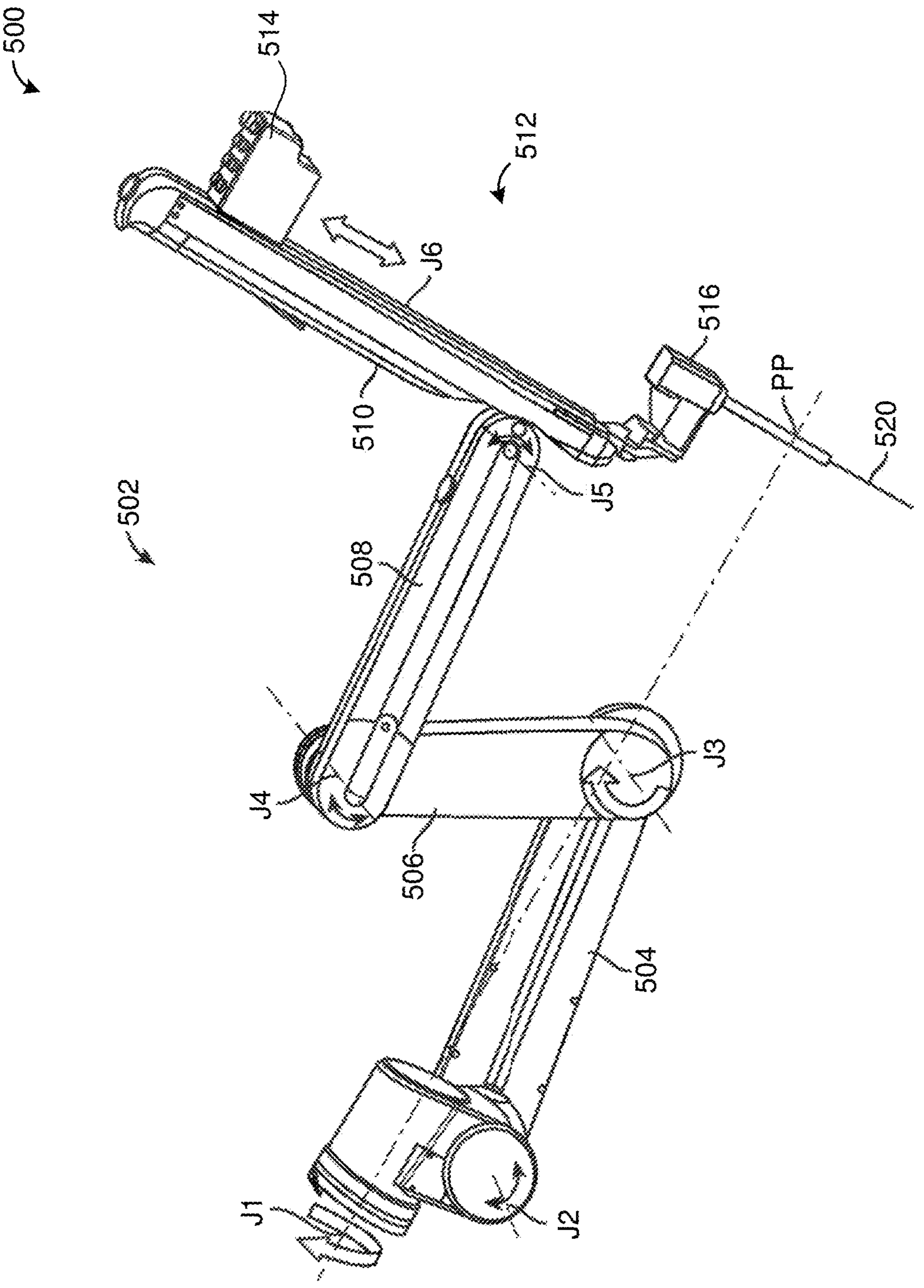
FIG. 5 shows an example of a manipulator assembly, in accordance with one or more embodiments.

An example of a manipulator assembly (500) in accordance with embodiments of the present disclosure is shown in FIG. 5. A manipulator assembly (500) includes a manipulator arm (502) and may further include a tool (520) (also called instrument (520)) (in FIG. 5, only an axis of the tool (520), but not the tool (520) itself, is shown). In other words, the manipulator assembly (500) may be the manipulator arm (502) with the tool (520) in some embodiments, and without the tool (520) in other embodiments. Other components may be included in the manipulator assembly (500). As described above, during operation, the manipulator arm (502) generally supports a distal instrument or tool (520) and effects movements of the tool (520). As a number of different tools (520) having differing end effectors may be sequentially mounted on a manipulator arm (502) or as a tool (520) needs to be removed and reinstalled during a procedure, a distal tool holder facilitates removal and replacement of the mounted instrument or tool (520). As may be understood with reference to FIG. 4, manipulator arms (502) are proximally mounted to a base of the robotic assembly. Alternatively, manipulator arms (502) may be mounted to separate bases that may be independently movable, e.g., by the manipulator arms (502) being mounted to single-manipulator arm carts, being provided with mounting clamps that allow mounting of the manipulator arm (502) directly or indirectly to the operating table (shown in FIG. 1A) at various locations, etc. Typically, a manipulator arm (502) includes a plurality of manipulator arm segments and associated joints extending between the proximal base and the distal tool holder.

In embodiments such as shown for example in FIG. 5, a manipulator arm (502) includes multiple joints (such as revolute joints J1, J2, J3, J4, and J5, and prismatic joint J6) and links or manipulator arm segments (504, 506, 508, and 510) The joints of the manipulator arm (502), in combination, may or may not have redundant degrees of freedom. A manipulator arm with one or more redundant degrees of freedom has a plurality of joints such that the plurality of joints may be driven into a range of differing configurations for a given position and/or orientation of a portion of the manipulator arm. For example, the manipulator arm (502) of FIG. 5 may be maneuvered into differing configurations while the distal member (512) supported within the tool holder (510) maintains a particular state and may include a given position or velocity of the end effector. The tool holder (510) may include a cannula (516) through which the tool shaft of the tool (520) extends, and the tool holder (510) may include a carriage ((514) shown as a box-shaped structure that translates on a spar) to which the tool attaches before extending through the cannula (516) toward the worksite.

Actuation of the degrees of freedom of the tool (520) is often provided by actuators of the manipulator. These actuators may be integrated in the carriage (514). A distal wrist of the tool (520) may allow pivotal and/or linear motion of an end effector of the tool (520) about tool joint axes of one or more joints at the tool wrist. An angle between end effector jaw elements may be controlled independently of the end effector location and orientation. A detailed description of the tool (520) is provided below with reference to FIG. 6.

Figure 6:
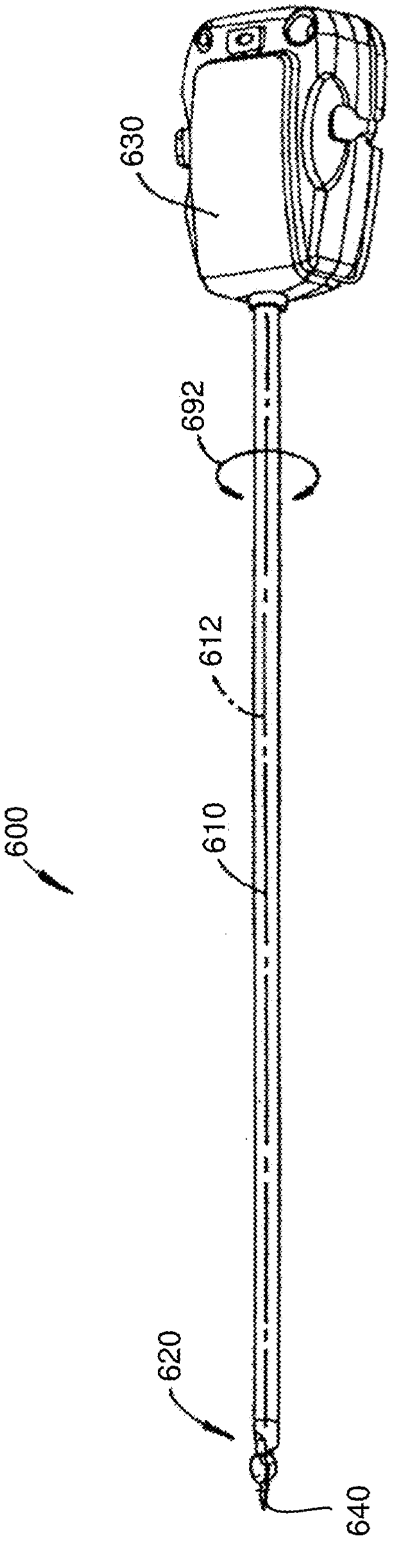
FIG. 6 shows a perspective view of a tool or instrument, in accordance with one or more embodiments.

FIG. 6 shows an example of a tool (600) (also called instrument (600)) as it may be used for surgery, in accordance with one or more embodiments. The tool (600) includes a shaft (610), a wrist (620) located at a working end of the shaft (610), and an end effector (640) disposed on the wrist (620). The wrist (620) may enable a pivoting of the end effector (640) relative to the shaft (610). The wrist (620) may have at least one degree of freedom. A housing (630), arranged releasably to couple the tool (600) to manipulator arm (502), is located at an opposed end of the shaft (610). The shaft (610) may be rotatably coupled to the housing (630) to enable angular displacement of the shaft (610) relative to the housing (630) as indicated by arrows (692) thereby allowing a rotation of the end effector (640) coupled to the shaft via the wrist (620). In FIG. 5, when the tool (520) is coupled or mounted on the manipulator arm (502), the shaft (610) extends through the cannula (516). The tool (520) typically is releasably mounted on a tool holder (510) of the manipulator arm (502), which may be driven to translate along a linear guide formed by prismatic joint (J6). Returning to FIG. 6, this may also be referred to as the IO, in/out movement, or insertion axis (612). The housing (630) may include spools that are rotatable to control cables to actuate linkages of the end effector (640), as described in U.S. Pat. No. 6,394,998, entitled "Surgical Tools for Use in Minimally Invasive Telesurgical Applications". The tool holder (510) of the manipulator arm (502) may include disks for coupling with the spools to drive the spools upon connection of the tool (600) to the manipulator arm (502). The disks may be driven by actuators, e.g., electrical motors, which respond to inputs from the associated input control devices (e.g. input control devices (210) in FIG. 2) to drive the end effector (640) to a desired orientation as dictated by movement of the input control devices (210) or any other control signal. Furthermore, appropriately positioned sensors, e.g., encoders, potentiometers, etc., may be provided to enable measurement of the joint positions. The actuators and sensors may be disposed in the carriage (514) of the tool holder (510), shown in FIG. 5.

Different tools (600) may be equipped with different end effectors (640) with different geometries, degrees of freedom, and/or functions. An end effector may have a single member or two or more members. Examples for end effectors with a single member include, but are not limited to, scalpels, cautery electrodes, irrigation or suction devices, endoscopes (which may or may not have a wrist), etc. Examples for end effectors with two members include, but are not limited to forceps, clip appliers, scissors, dissection tools, pliers, or the like. Members of the end effector (640) may be individually angularly displaceable, thereby not only allowing an opening and closing of the end effector, but also enabling an angular displacement to change the orientation of the end effector (640) as a whole, relative to the wrist (620).

While FIG. 1A, FIG. 1B, FIG. 2, FIG. 3, FIG. 4, FIG. 5, and FIG. 6 show various configurations of components, other configurations may be used without departing from the scope of the invention. For example, various components may be combined to create a single component. As another example, the functionality performed by a single component may be performed by two or more components. Further, while the components are described in context of surgical scenarios, embodiments of the disclosure may be equally applicable to other domains that involve robotic manipulation.

Figure 7A:
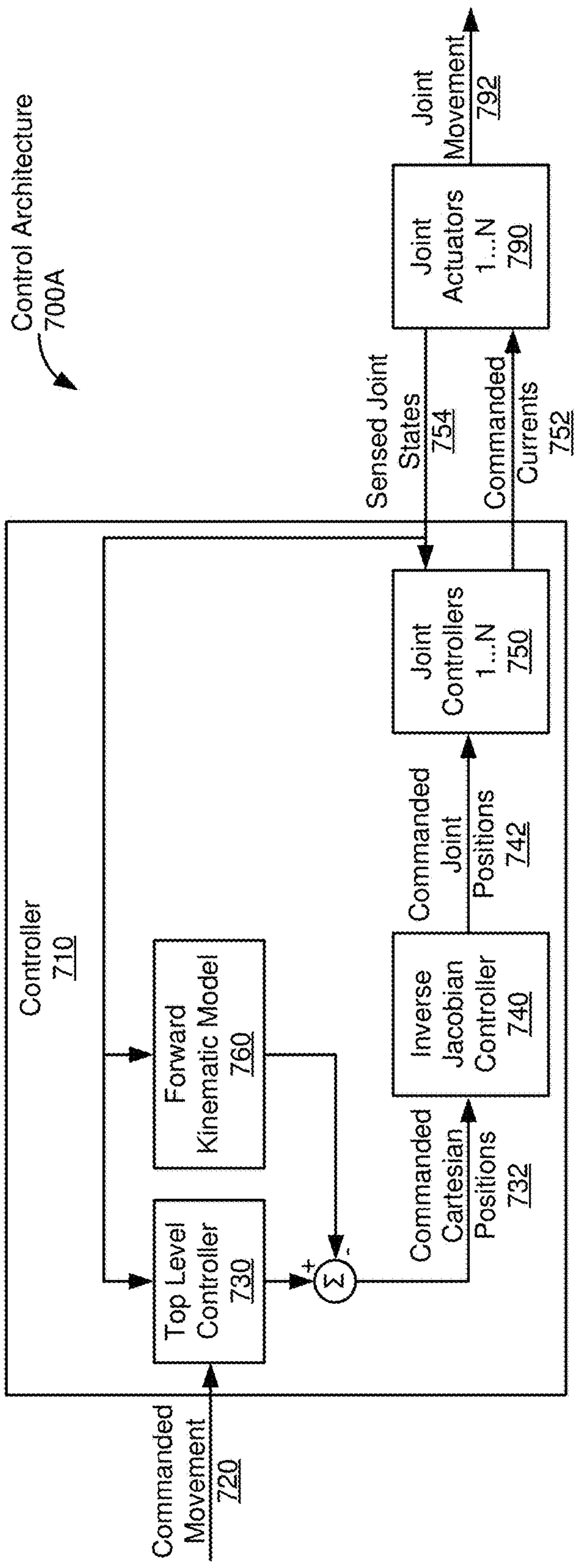
FIG. 7A and FIG. 7B show control architectures for controlling a robotic assembly, in accordance with one or more embodiments.

Turning to FIG. 7A, a control architecture for controlling a manipulator assembly including a manipulator arm and an instrument or tool mounted thereon, in accordance with one or more embodiments, is shown. One control architecture is illustrated as an example. Those skilled in the art will appreciate that other control architectures may be used without departing from the disclosure. Further, in the illustrated control architecture, particular signals (e.g. positions) are exchanged between blocks of the control architecture. Other signals (e.g., velocities, accelerations, forces, etc.) may be used, without departing from the disclosure. Also, the control architecture may implement different modes (not shown). For example, during a robotic task being performed under the control of input control devices (210) operated by a user as shown in FIG. 2, various joints of the robotic manipulator assembly may be position-controlled. Also, in another control mode, e.g., during a tool exchange mode, one or more of the joints may be "floating", allowing an assistant to readily externally articulate these one or more joints, such as by back-driving these one or more joints. A floating joint may be back-driven by an externally applied force without a control algorithm counteracting the back-driving or a braking force configured to counteract such back-driving. For example, a floating joint may be controlled to be in a "clutch mode" in which the commanded position for the floating joint is the current position to assist external manipulation. As a further example, a user may apply a force to a link distal to the floating joint, causing the back-driving of the floating joint. A floating joint, in particular when the joint may move in a gravitational pull direction (e.g., axis of the joint is non-vertical), may further be gravity-compensated. In addition, a friction compensation may facilitate the back-driving. Additionally or alternatively, a floating joint may also be controlled to impose other characteristics such as a certain level of damping.

Multiple control modes may be combined during operation of the manipulator assembly, e.g., some joints may be position controlled to resist or rebound from external articulation of those joints, while other joints may be floating and facilitate external articulation of those other joints. In addition, one or more joints of the manipulator assembly may be passive, i.e., not position or velocity controlled at all (but may be with brakes partially or completely applied). Passive joints may be manually operated. Passive joints may also include joint sensors, such that the full kinematics of the manipulator assembly may be obtained. Further, in some embodiments, passive joints may contain actuators for supplying gravity compensation, friction compensation, or other utility not including actively driving the motion of the passive joint.

In one or more embodiments, the joint movements of the manipulator assembly are controlled by driving one or more joints by a controller using actuators (e.g., motors, solenoids, etc.) of the manipulator assembly, the joint movements being calculated by a processor of the controller. Mathematically, the controller may perform at least some of the calculations of the joint commands using vectors and/or matrices, some of which may have elements corresponding to positions, velocities, and/or forces/torques, etc. of the joints. The range of alternative joint configurations available to the processor may be conceptualized as a joint space. The joint space may, for example, have as many dimensions as the manipulator assembly has degrees of freedom, and a particular configuration of the manipulator assembly may represent a particular point in the joint space, with each coordinate corresponding to a joint state of an associated joint of the manipulator assembly.

As used herein, the term "state" of a joint or multiple joints refers to the control variables associated with the joint or the multiple joints, respectively. For example, the state of an angular joint may refer to the angle defined by that joint within its range of motion, and/or to the angular velocity of the joint. Similarly, the state of an axial or prismatic joint may refer to the joint's axial position, and/or to its axial velocity. While one or more of the controllers described herein include position controllers, they often also have velocity control aspects. Alternative embodiments may rely primarily or entirely on velocity controllers, force controllers, acceleration controllers, etc. without departing from the disclosure. Many aspects of control systems that may be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, etc.

The control architecture (700A) of FIG. 7A includes a controller (710) that drives joint actuators (790) of the manipulator assembly based on a commanded movement (720). Any number of joint actuators (790) may be driven.

The commanded movement (720) may be a commanded position and/or velocity of one or more features in the work-space, in Cartesian-coordinate space (referred to herein as Cartesian-space). The commanded movement (720) may be, for example, a movement command (e.g., in the form of a position and/or velocity) received from the user control system (120), or any other movement command of one or more features of the manipulator arm. A feature may be any feature physically on the manipulator assembly or physically off the manipulator assembly, which may be used to define a control frame to be articulated using control inputs. Examples of features on the manipulator assembly include features of a tool (e.g., an end effector tip, a central point on the end effector, or a clevis of the end effector), a feature of the manipulator arm (e.g., an instrument holder configured to physically couple with a removable instrument), etc. Another example of a feature of the manipulator assembly is a reference point in empty space which is exactly a certain distance and angle away from the tool-tip. Another example of a feature off the manipulator assembly is a target tissue whose position relative to a part of the manipulator assembly may be established.

The controller (710) may include a top level controller (730), an inverse kinematics controller (740), joint controllers (750), and a forward kinematics model (760). Each of these components is subsequently described.

The top level controller (730), in accordance with one or more embodiments, includes instructions in the form of computer readable program code to receive the commanded movement (720), and to convert the commanded movement (720) into positions in a Cartesian reference frame. The steps performed to convert the commanded movement (720) into Cartesian positions depend on the format in which the commanded movement (720) is provided. For example, if the commanded movement (720) specifies a desired end effector position, the top level controller (730) may perform trajectory planning using, for example, a position-time (PT) or position-velocity-time (PVT) interpolation. Alternatively, if the commanded movement (720) includes a velocity command, the top level controller (730) may operate as an integrator. Those skilled in the art will appreciate that the top level controller (730) may perform any operation necessary to obtain a position signal in a Cartesian reference frame. In one or more embodiments, the top level controller (730) generates the Cartesian positions from the commanded movement (720) under consideration of the commanded joint positions (742). The commanded joint positions (742) may enable the top level controller to determine an actual state (e.g., including current position and/or velocity, etc.) of the joints to be controlled. The actual state may affect the control task and, therefore, may be considered by the top level controller. For example, for a particular configuration of the manipulator assembly, a commanded movement may be undesirable or unsafe and may, thus not be executed or alternatively may be converted into an alternative commanded movement that may be safely executed.

The inverse kinematics controller (740), in accordance with one or more embodiments, includes instructions in the form of computer readable program code to convert commanded Cartesian positions (732) into commanded joint positions (e.g., joint angles for rotary joints) (742). The operations by the inverse kinematics controller may be performed in the velocity domain. In other words, the inverse kinematics controller (740) may seek to determine or solve for a joint velocity vector that may be used to drive the joints of the manipulator assembly in such a way that the end effector accurately follows the commanded Cartesian positions. The inverse kinematics controller (740) may integrate the computed joint velocities to obtain command joint positions (742).

The Cartesian error (732) may be a combination of the Cartesian positions provided by the top level controller (730), as previously discussed, and Cartesian positions provided by a forward kinematics model (760), discussed below. More specifically, the Cartesian positions provided by the forward kinematics model (760) may represent an estimate of an actual or current position (e.g., of an end effector), in Cartesian space, of the manipulator assembly. This estimate may be subtracted from the Cartesian positions representing the commanded movement, to obtain the difference to be compensated for, to be used as the control input to the inverse kinematics controller (740).

While generally there may not be a closed form relationship which maps a desired Cartesian space position to an equivalent joint-space position, a closed form relationship between the Cartesian space velocity and joint-space velocities typically exists. The kinematic Jacobian is the matrix of partial derivatives of Cartesian space position elements with respect to joint space position elements. In this way, the kinematic Jacobian captures the kinematic relationship between, for example, the end effector and the joints. In other words, the kinematic Jacobian captures the effect of joint motion on the end effector. The kinematic Jacobian (J) may be used to map joint-space velocities (dq/dt) to Cartesian space velocities (dx/dt), e.g., end effector velocities.

Thus, even when there is no closed-form mapping between input and output positions, mappings of the velocities may iteratively be used by the inverse kinematics controller (740) to implement a movement of the manipulator assembly based on a commanded trajectory. One such implementation is subsequently described in simplified terms. Assume that the commanded movement (720) includes Cartesian positions provided at time steps, ti. At each time step (ti), a Cartesian velocity (dx/dt) is calculated by the inverse kinematics controller (740) to perform the desired movement and to correct for built up deviation from the desired Cartesian position (obtained by the subtraction of the Cartesian position produced by the forward kinematics model (760)). This commanded Cartesian position (or Cartesian error (732), after subtraction of the output of the forward kinematics model) is then converted into a commanded joint position (q) (742) using the pseudo-inverse of the Jacobian (J #), in the velocity domain. The commanded joint position is used to re-calculate the Jacobian (J), which may be used for the calculations performed for the next time step. The described steps may be performed for any number of joints.

Some of the example manipulator assemblies described herein have more degrees of freedom than are needed to position and move an end effector within a worksite. For example, a surgical end effector that may be positioned with six degrees of freedom at an internal surgical site through a minimally invasive aperture may in some embodiments have a nine degrees of freedom task space (six end effector degrees of freedom-three for location, and three for orientation-plus three degrees of freedom to comply with the access site constraints), but may have ten or more degrees of freedom. Highly configurable manipulator arm assemblies having more degrees of freedom than are needed for a given end effector position may be described as having or providing sufficient degrees of freedom to allow a range of joint states for an end effector position in a workspace. For example, for a given end effector position, the manipulator assembly may occupy (and be driven between) any of a range of alternative manipulator arm configurations. Similarly, for a given end effector velocity vector, the manipulator assembly may have a range of differing joint movement speeds for the various joints of the manipulator assembly within the null-space of the Jacobian.

When directing movement of highly configurable manipulators with redundant degrees of freedom, the inverse Jacobian generally does not fully define a joint vector solution. For example, the mapping from a Cartesian command (x) to joint position (q) in a system that may occupy a range of joint states for a given end effector state is a mapping of one-to-many. In other words, because the mechanism is redundant, there are a mathematically infinite number of solutions, represented by a subspace in which the inverse lives. Additional constraints may be imposed to arrive at a unique solution. Those skilled in the art will appreciate that various methods may be used to perform inverse kinematics, including inverse kinematics for manipulators with and without redundant degrees of freedom.

Each of the joint controllers (750), in accordance with one or more embodiments, includes instructions in the form of computer readable program code to convert a received commanded joint position (742) into a commanded current (752) to drive one of the joint actuators (790) producing a joint movement (792). One joint controller (750) may be used per joint actuator (790). The joint movements (792) of all joint actuators through the kinematics of the manipulator assembly may produce a manipulator arm movement that reflects the commanded movement (720). In one embodiment of the disclosure, the joint controller controls a joint position or angle. Alternatively, the joint controller may control other variables such as joint velocity, joint torque or joint force (in case of a linear joint). An example of a joint controller (750) is provided in FIG. 7B.

The forward kinematics model (760), in accordance with one or more embodiments, includes instructions in the form of computer readable program code to convert the sensed joint positions (754) into Cartesian positions, as previously discussed.

The controller (710) may be implemented on one or more computing systems. These one or more computing systems may be based on digital signal processors (DSPs), central processing units (CPUs), etc. An example computing system is described with reference to FIG. 1B. Each of the computing systems may perform the described operations at a cycle time that depends on the nature of the operations. In one embodiment, the cycle times of the inverse kinematics controller (740) and the joint controllers (750) are identical. The communication between the computing systems implementing the top level controller (730), the inverse kinematics controller (740), and the joint controllers (750) may be performed using any type of electrical or optical communication networks, including Ethernet, fiber optics, various bus systems, and/or any other type of digital or analog signals.

Figure 9:
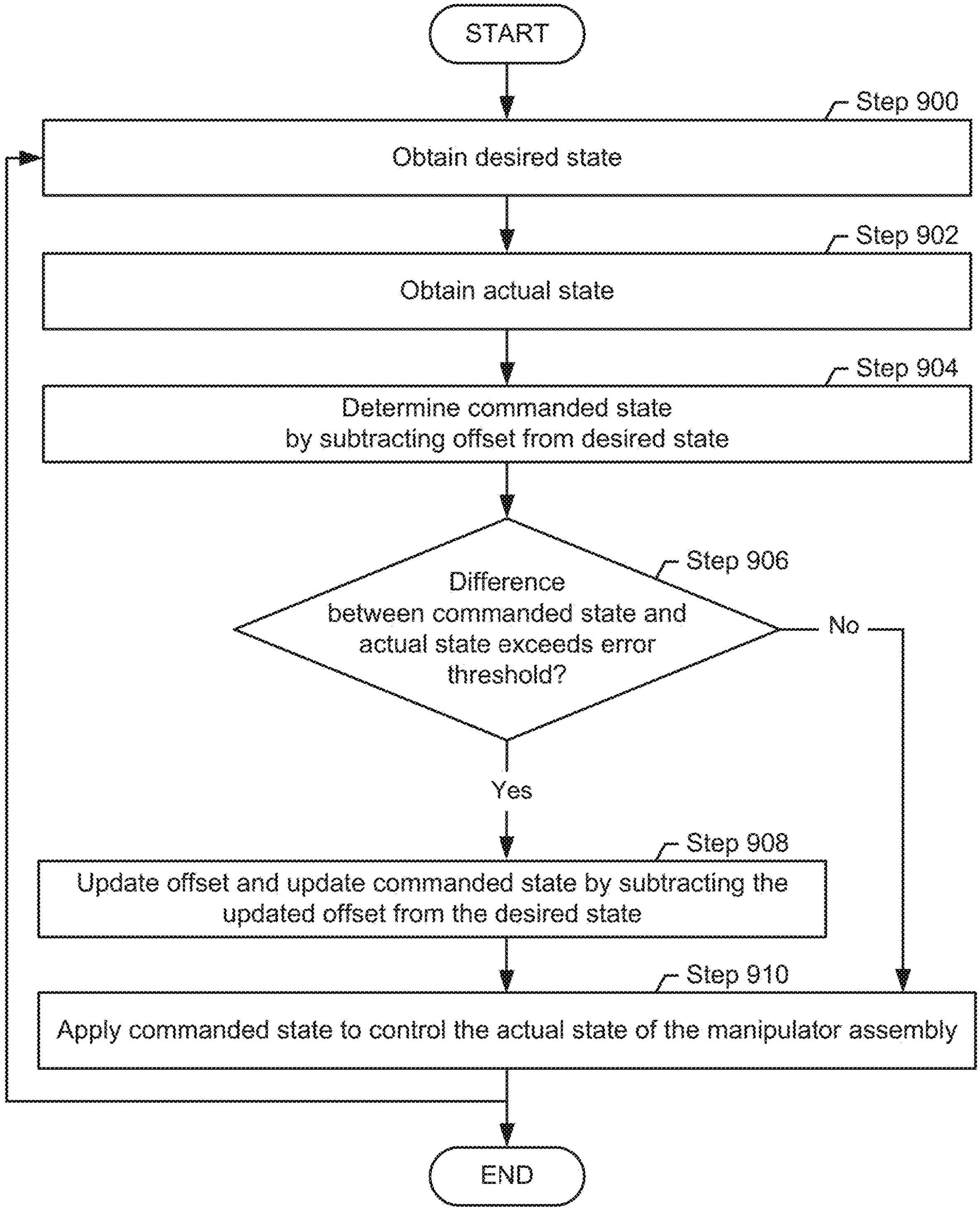
FIG. 9 shows a flowchart describing a method for limiting or reducing an energy buildup in a servo-controlled mechanism, in accordance with one or more embodiments.

In one or more embodiments, the controller (710) is further configured to perform at least one of the steps described in FIG. 9.

Figure 7B:
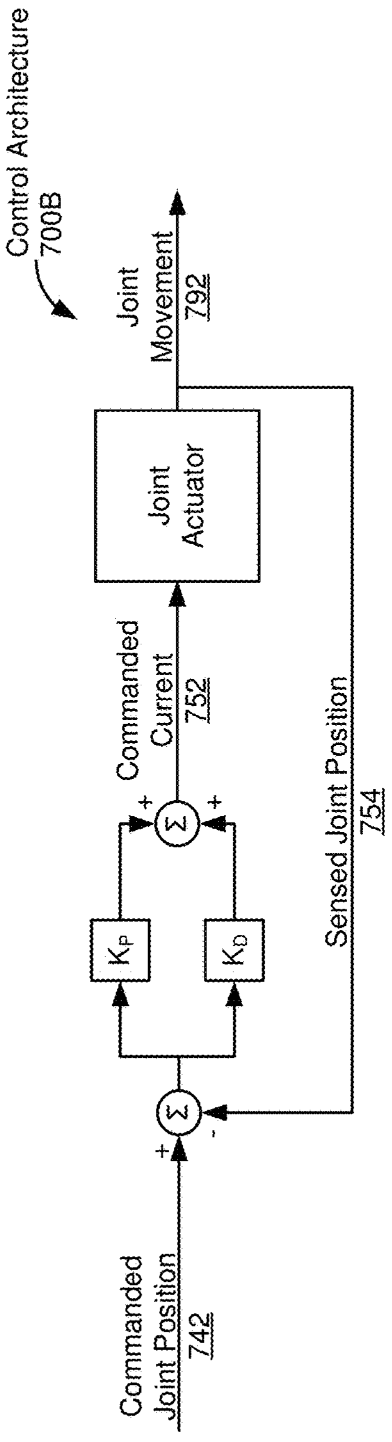

Turning to FIG. 7B, a control architecture (700B) of a joint controller, in accordance with one or more embodiments, is shown. In the example, a closed-loop PD control structure is used to control a joint position based on a commanded joint position input.

The joint controller may receive a feedback signal in the form of a sensed joint state (754) (specifically, in this example, a sense joint position), in case of the control architecture (700B)) from the associated joint actuator (790) to enable closed-loop control. The sensed joint position comprising the joint state (754) may be derived from signals obtained from a sensor attached to the joint. Such a sensor may be, for example, an incremental encoder, a shape sensor, or a hall sensor of the joint or joint actuator. A state observer or estimator (not shown) may be used. The PD control structure uses two control gains ($K_P$, $K_D$), operating on a difference between the commanded joint position (742) and the sensed joint position (i.e. an error signal) and their derivatives, respectively, to produce a commanded current (752). In one or more embodiments of the disclosure, the commanded current (752) is limited, and accordingly the resulting joint torque or force is limited as well. The limit may be based on hardware limitations such as a maximum acceptable motor current. The limit may further be software configurable.

Accordingly, the motor current (and the resulting motor torque or force) may increase linearly with the position error between the commanded joint position (742) and the sensed joint position (754) as dictated by the proportional control gain ($K_P$) only until the saturation limit is reached. Beyond the limit, the motor current is constant. A higher $K_P$ may result in a relatively small position error being sufficient for reaching the saturation limit, whereas a lower $K_P$ may result in a relatively larger position error being required for reaching the saturation limit. In one embodiment of the disclosure, a relatively high $K_P$ is used to obtain a responsive position control of the joint with a limited steady state error. Accordingly, an increase in the position error may quickly result in reaching the saturation limit. While the control architecture (700B) uses a proportional derivative (PD) controller, other controllers such as proportional integral derivative (PID), full state feedback, sliding mode, or various other control schemes, may be used, without departing from the disclosure. Further, while the control of a joint position is illustrated, other variables such as velocity, torque or force may be controlled, without departing from the disclosure.

The nature of the command signal may further change during the operation. For example, during a robotic task being performed under the control of input control devices (210) operated by a user as illustrated in FIG. 2, various joints of the robotic manipulator assembly may be position-controlled. However, in another control mode, e.g., during a tool exchange, one or more of the joints may be "floating", allowing an assistant to freely back-drive these joints. In this mode, the one or more joints may still be position-controlled, although with the commanded joint position (742) being the sensed joint position (754).

Figure 8:
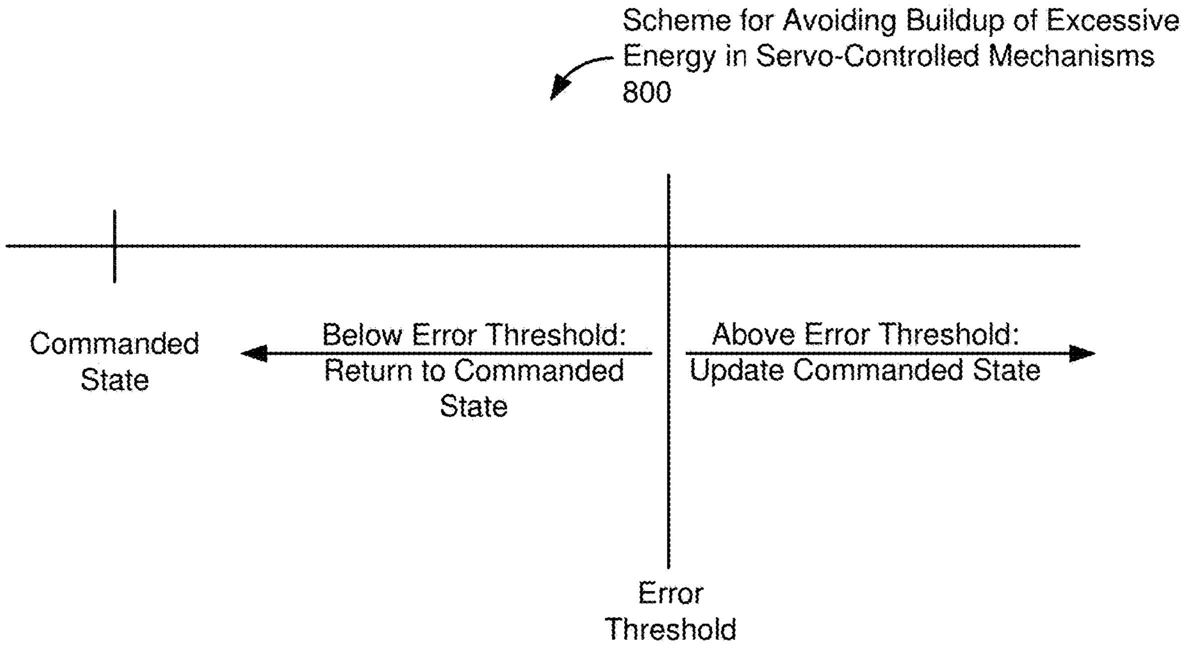
FIG. 8 shows a diagram that conceptually illustrates an approach for avoiding a buildup of excessive energy in servo-controlled mechanisms, in accordance with one or more embodiments.

Turning to FIG. 8, a diagram that conceptually illustrates an approach for avoiding a buildup of excessive energy in servo-controlled mechanisms (800) is shown.

Assume that PD controllers, as introduced in FIG. 7B, are used for the control of the joint actuators of a manipulator arm or a manipulator assembly including the manipulator arm and a tool. One PD controller may be used per joint actuator of a manipulator arm segment. As discussed with reference to FIG. 7B, the proportional control gain of the PD controller may operate on the difference between the commanded position and the sensed joint position to generate a commanded current driving the joint actuator, and the joint actuator may produce a torque that is proportional to the commanded current. Accordingly, a larger difference between the commanded joint position and the sensed joint position results in a stronger torque produced by the joint actuator. Thus, a PD controller-based control loop may have characteristics of a linear spring: The farther apart the commanded and the actual joint positions are, the more energy is stored in the spring, due to the PD controller's increased effort to compensate for the difference. The coefficient of the spring may be governed by the proportional control gain ($K_P$).

While the difference between the commanded joint position and sensed joint position typically results in the commanded current that causes a compensation for the difference by driving the joint actuator in a direction countering the difference, under certain circumstances that compensation may not occur. Assume for example, that (a) a manipulator arm segment attached to the joint with the actuator encounters an obstacle blocking movement, or (b) the manipulator arm segment attached to the joint with the actuator is back-driven by a user. In either scenario, the difference between the commanded joint position and the sensed joint position is prevented from being reduced and may even increase. As a result, in scenario (a), when the obstacle is removed, the manipulator arm may move abruptly. The abrupt movement may surprise or startle the user, may cause potentially forceful collisions, etc. In scenario (b), as soon as the user stops the back-driving of the manipulator arm, the manipulator arm may return to the commanded position, even though the user may have intentionally back-driven the manipulator arm under the assumption that the back-driven manipulator arm would remain in the back-driven position. The user may have had various reasons for back-driving the manipulator arm, for example when trying to avoid a hazardous or inconvenient position.

To address the undesirable buildup of an excessive discrepancy between commanded and sensed joint positions, the approach for avoiding or limiting a buildup of excessive energy in servo-controlled mechanisms, introduced in FIG. 8, may be used. Specifically, as FIG. 8 shows, an error threshold is used to determine whether a discrepancy between a commanded and a sensed joint position (or more generally, between a commanded joint state and an actual joint state) is acceptable or not. The error threshold may be set with respect to a commanded position or, more generally, a commanded state. If the difference between the commanded state and the actual state exceeds the error threshold, the commanded state may be updated to be closer to the actual state, thereby reducing the difference to an acceptable level, below the error threshold. In contrast, if the difference between the commanded state and the actual state is below the error threshold, the commanded state may not be updated.

Referring to the previously introduced scenarios (a) and (b), the implications are as follows. For (a), while the obstacle is present, thereby blocking movement of the manipulator arm segment, the joint actuator may produce a force operating against the obstacle. The force may be a result of the maximum force (or torque) produced by the joint(s) when reaching the saturation limit, because the saturation limit of the joint(s) limits the commanded current even if a positional error, through $K_P$. would hypothetically produce a higher commanded current. Once the obstacle is removed, only a limited movement of the link may result due to the updating of the commanded joint position to be in proximity to the sensed joint position. This movement may be almost imperceptible. Accordingly, removal of the obstacle does not result in undesirable consequences such as abrupt movement of the link. For (b), the manipulator arm segment may be back-driven and may remain in or close to the back-driven position, based on the updating of the commanded state.

While the above discussion introduces the approach for avoiding a buildup of excessive energy in servo-controlled mechanisms using position control based on a difference between a commanded position and an actual position of a joint, those skilled in the art will appreciate that similar paradigms apply to other configurations. For example, an alternative configuration may apply to velocity-controlled joints. Further, while the above discussion is based on the control of a joint or joints, with the variables being considered (e.g., commanded joint position, actual joint position) being in a joint reference frame, the method may also be applied in a Cartesian reference frame, e.g., when applying a similar paradigm to an entire manipulator arm, as discussed below.

FIG. 9 shows a flowchart in accordance with one or more embodiments. The flowchart of FIG. 9 depicts a method for reducing or limiting an energy buildup in servo-controlled mechanisms while in a non-clutch mode, in accordance with one or more embodiments. The non-clutch mode may be used to perform any tasks involving servo control of one or more joints of a manipulator arm, such as position holding tasks, teleoperation (i.e., "following") tasks, and positioning tasks; these tasks may involve manipulation or imaging of the environment using the manipulator assembly. One or more of the steps in FIG. 9 may be performed by various components of the systems, previously described with reference to FIGS. 1A, 1B, 2, 3, 4, 5, and 6. These figures describe particular manipulator arms and particular tools, the manipulator arms and tools having certain degrees of freedom. However, the subsequently described methods are not limited to a particular configuration of manipulator arms, tools and/or degrees of freedom. Instead, the methods are applicable to any type of manipulator arm, paired with any type of tool, used in any type of scenario. Further, the described methods may be applied to various signals and spaces. For example, the method may be applied to position, velocity, or force signals, in joint space and/or in Cartesian space. To further illustrate the application of the method, examples are provided in FIGS. 10A, 10B1, and 10B2. A discussion of various applications and benefits follows.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 9.

Turning to the flowchart of FIG. 9, a series of steps which, when executed repeatedly, may form a servo loop for servoing at least one joint of a manipulator arm assembly, are shown. The servoing may put the manipulator assembly into a manipulation mode, allowing the manipulator assembly to perform a robotic task. The control of a manipulator arm or a manipulator assembly may involve a hierarchy of such control loops. As previously shown in FIG. 7A, one control loop may be used to produce commanded joint positions from a commanded movement, provided as an input. Further, as previously shown in FIG. 7B, additional control loops may be used on a joint level to convert the commanded joint positions into commanded currents to drive the joint actuators. Methods for reducing an energy buildup in servo-controlled mechanisms may be integrated with these control loops in various ways, as subsequently described.

In Step 900, a desired state is obtained. The desired state may be for one or multiple joints associated with one or more manipulator arm segments of the manipulator assembly, or for the entire manipulator assembly. The desired state may be a desired position, a desired velocity, a desired force, etc. Depending on the implementation of the method for reducing an energy buildup, the desired state may be provided in a Cartesian reference frame or in a joint reference frame.

In an implementation that applies the method for reducing an energy buildup to the entire manipulator assembly or to multiple manipulator arm segments of the manipulator assembly, the desired state may be provided in a Cartesian reference frame, for example to direct an end effector of the manipulator assembly. In such an implementation, the commanded state may affect the state of multiple (or all) manipulator segments and their associated joints, based on the control architecture shown in FIG. 7A.

In an implementation that applies the method for reducing an energy buildup to one or more manipulator arm segments on a joint level, the desired state may be provided in joint reference frames to direct the affected manipulator arm segments by controlling the associated joints' position, angle, torque, or force, based on the control architecture shown in FIG. 7B.

In Step 902, an actual state is obtained. The actual state may be an actual position, an actual velocity, an actual torque, an actual force, etc. In one or more embodiments, the actual state, used for the subsequent steps, is represented by a sensed state. The sensed state may be obtained from sensors, e.g., sensors in the joint actuators. Thus, the sensed state may be a measurement of the actual state. The sensed state may alternatively be an estimate of the actual state. For the purpose of the subsequent discussion, the sensed/estimated state and the actual state are treated as equivalents. Depending on the implementation of the method for reducing an energy buildup, the actual state may be provided in a Cartesian space or in a joint space.

In an implementation that applies the method for reducing an energy buildup to the entire manipulator assembly or to multiple manipulator arm segments of the manipulator assembly, the actual state may be provided in a Cartesian space. The actual state may represent, for example, a position, a velocity, a force, or a torque of the end effector of the manipulator assembly. In this implementation, to obtain the actual state, individually sensed joint states (e.g., joint positions or velocities) may be used to reconstruct the state of the manipulator arm assembly in the Cartesian space.

In an implementation that applies the method for preventing an energy buildup to one or more manipulator arm segments on a joint level, the actual state may be provided in the joint space of the joint(s) under consideration, reflecting the state(s) of the associated manipulator arm segment(s).

In Step 904, a commanded state is obtained. The commanded state, in accordance with one or more embodiments, is obtained by subtracting an offset from the desired state. The offset may reflect the difference between the desired state and the actual state, obtained during a previous execution of Step 908 of the method of FIG. 9, as described below. Initially, the offset may be zero, such that the commanded state is equal to the desired state. However, over time, as the method of FIG. 9 addresses energy buildups (resulting from discrepancies between the commanded state and the actual state), the offset may increase or decrease.

In Step 906, the difference between the commanded state and the actual state is compared against an error threshold to determine whether the difference exceeds the error threshold. The absolute difference may be used to make the determination regardless of whether the difference is positive or negative. The error threshold may have been previously established. A reduced error threshold may be preferred for scenarios in which less energy buildup can be accepted, whereas an increased error threshold may be used in scenarios in which more energy buildup can be accepted. An increased error threshold may also be used in scenarios where it is less desirable to alter the commanded state. If the difference reaches or exceeds the error threshold, the execution of the method may proceed with Step 908. If the difference is below the error threshold, the execution of the method may bypass Step 908 to proceed directly with Step 910.

In Step 908, an updated offset is obtained, and the commanded state is updated using the updated offset. In one or more embodiments, the updated offset is an offset that reduces the difference between the commanded state and the actual state, thereby reducing the energy buildup in the servo loop, associated with the proportional control gain $K_P$ operating on the difference between the commanded state and the actual state. More specifically, the updated offset may be computed to accomplish an adjustment of the commanded state toward the actual state, while not completely reaching it. The commanded state may, thus, end up in close proximity to the actual state. The resulting difference between the commanded state and the actual state may be barely sufficient to reach the saturation limit of the associated actuator, based on the proportional control gain ($K_P$) selected for the actuator, i.e., the commanded state may be set to the minimum distance (or a small multiple of the minimum distance) from the actual state required to obtain saturation. In other words, a barely sufficient difference between the commanded state and the actual state is a difference that drives the servo loop into saturation without the difference being significantly larger than necessary to reach the saturation limit. The updating of the commanded state may be performed in a single time instant or more gradually over time (e.g. over a fraction of a second or multiple seconds, etc.) in a single step or over multiple steps. A multi-step or more gradual updating may be more likely used with algorithms that check the commanded state for unexpected jumps (e.g. seemingly implausible jumps, such as jumps beyond what the system can achieve or an expected maximum for the operating condition). In such cases, a multi-step or more gradual updating would help avoid incorrectly triggering such algorithms. Multi-step or more gradual updating may also be more likely used in scenarios where a larger discrepancy between actual and commanded state has built up, such as may be more common during particular mode switches.

In Step 910, the commanded state is applied to control the actual state of the manipulator arm assembly. The control task of Step 910 may be performed by control architectures similar to the control architectures introduced in FIGS. 7A and 7B.

If the method of FIG. 9 is performed in Cartesian space, the entire control loop as shown in FIG. 7A may be affected by the commanded state. One or more of the joints of the manipulator assembly may be driven based on the commanded state. The manipulator assembly may, however, also include joints that are not affected by the commanded state, for example, passive joints (i.e., joints that are not equipped with a joint actuator).

Alternatively, if the method of FIG. 9 is performed in joint space, the control loop of the joint being controlled, as shown in FIG. 7A, may be affected by the commanded state. Multiple joints may be controlled, as described by FIG. 9, if the method of FIG. 9 is implemented for multiple joints.

Regardless of whether the described steps are executed for an entire manipulator assembly or for a single joint, reducing or limiting an energy buildup may reduce the likelihood of undesirable situations. More specifically, as a result of reducing the difference between the commanded state and the actual state (by setting the commanded state closer to the actual state) provided to the proportional control gain(s) of one or more joint actuators associated with the manipulator segment(s), the energy buildup in these manipulator segment(s) is limited. The limiting of the energy buildup may be used in conjunction with a variety of control tasks that may benefit (with the exception of control tasks that are specifically intended to facilitate external back-driving, such as the "floating" of one or more joints). Examples of control tasks that may benefit from the described methods for reducing or limiting an energy buildup in servo-controlled mechanisms include, but are not limited to, position holding tasks, teleoperation tasks, and positioning tasks, including positioning task that use position-time (PT) and position-velocity-time (PVT) interpolation. Two specific examples are subsequently described.

While the above description of the flowchart of FIG. 9 covers a method for servoing at least one joint of a manipulator arm assembly in a non-clutch mode, other methods may be executed for the same manipulator assembly without departing from the disclosure. In one embodiment of the disclosure, one or more of the joints of the manipulator assembly or the entire manipulator assembly may be operated in a clutch mode. Further, one or more joints may be in clutch mode while other joints may be in manipulation mode. In the clutch mode, one or more of the joints may be "floating", allowing an assistant to readily externally articulate these one or more joints such as by back-driving these one or more joints. A floating joint may be back-drivable by an externally applied force without a control algorithm counteracting the back-driving. For example, a user may apply a force to a link distal to the floating joint, causing the back-driving. As previously discussed, a floating joint may be gravity and/or friction compensated to further facilitate the back-driving. Various clutch modes may be implemented. In one embodiment of the disclosure, the clutch mode allows the user to move the remote center of the manipulator arm, while allowing or preventing movement of the end effector. In one embodiment of the disclosure, the clutch mode allows the user to move at least some joints of the manipulator arm while preventing movement of the tool or end effector. Combinations of the described clutch modes and additional clutch modes may be implemented for the manipulator assembly without departing from the disclosure.

The following examples are for explanatory purposes only and not intended to limit the scope of the disclosure. FIG. 10A schematically shows a manipulator assembly (1000) in a position holding task (i.e., with the controller in a manipulation mode in which the manipulator assembly is servo-controlled to hold a position), in accordance with one or more embodiments. In the position holding task, the manipulator assembly is controlled to remain stationary at a commanded position (1002) (manipulator assembly configuration at commanded position shown using dashed lines). Referring to the configuration shown in FIGS. 1A and 1B, a position holding task may be used during phases of a robotic task in which no input is provided by the user control system (120) (e.g., because the manipulator assembly is not currently under teleoperative control), while requiring the manipulator assembly to remain stationary. Accordingly, in absence of external perturbations, the commanded position is held. In FIG. 10A, an external force (1004) is applied, back-driving the manipulator assembly. The actual position, therefore, becomes a back-driven position (1006) (manipulator assembly configuration at actual position shown using solid lines). When the manipulator assembly is back-driven by an external force, energy begins to build up in the joints of the manipulator assembly, as the actual positions of the joints deviate from the joint positions necessary to hold the commanded position. Once the error threshold is exceeded due to the back-driving, the commanded position is updated. In the example of FIG. 10A, the commanded position is updated to be near the back-driven position (1006). Accordingly, the joint actuators, even in the back-driven position (1006) may still produce maximum torques/forces, based on the joint actuators' saturation limits being reached due to the small remaining difference between the updated commanded position and the back-driven position. Once the back-driving ceases, the manipulator arm may perform a small movement to reach the updated commanded position. The small movement may be barely perceptible by an operator observing the manipulator arm, or be considered small and acceptable by the operator given the operational context. While, in the example, the position holding task is described within the context of an end effector controlled in a Cartesian space, the position holding task may be performed in a similar manner for single joints.

The described method may be particularly beneficial when switching to a control mode that implements the method for limiting an energy buildup, in accordance with one or more embodiments, from a control mode that does not implement this method. Assume, for example, that a manipulator joint is controlled in a teleoperation mode (e.g., using input provided by a user via the input control devices). Further, assume that the teleoperation mode does not implement the method for limiting the energy buildup. When switching to a control mode that does implement the method for limiting the energy buildup (e.g., a holding mode), excessive energy in the control loop is dissipated. More specifically, a possible discrepancy between an actual position and a commanded position that exceeds the difference providing joint torque saturation is reduced to a level that is barely sufficient to maintain the saturation. Accordingly, the joint torque remains constant during the switching (the joint torque is in saturation before and after the switching), yet the excessive energy buildup is dissipated.

FIG. 10B1 schematically shows a manipulator assembly (1050) in a teleoperation (i.e., "following") task and FIG. 10B2 shows a trajectory (1070) in a teleoperation task (for example, with the controller in a manipulation mode in which the manipulator assembly is servo-controlled to follow incrementally changing positions specified by the trajectory (1070)), in accordance with one or more embodiments. Consider, for example, the master-slave configuration as shown in FIGS. 1A and 1B, where the commanded trajectory, may be obtained from the input control devices (210) under teleoperative control of an operator, as shown in FIG. 2. The commanded trajectory may also be obtained from any other source. The commanded trajectory may be specified by at least a final point and may further include intermediate points. Position-time (PT) and position-velocity-time (PVT) path interpolation algorithms may be used to establish the commanded trajectory based on the specified points.

In the following task, the manipulator assembly is controlled to follow a commanded position (1052) (manipulator assembly configuration at commanded position shown using dashed lines). In FIG. 10B1, assume that the commanded position (1052) is just one point of a commanded trajectory. The next commanded position may be elsewhere to cause movement, or alternatively the next commanded position may be in the same position to keep the manipulator assembly stationary. In absence of external perturbations (such as obstacles), the manipulator assembly would reach the commanded position (1052).

However, in FIG. 10B1, an obstacle (1054) prevents the manipulator arm from reaching the commanded position (1052). The actual position of the manipulator assembly is stuck in a blocked position (1056) (manipulator assembly configuration in blocked position shown using solid lines). The commanded torque for the joint actuators of the manipulator assembly may saturate, as a result of the manipulator assembly being unable to reach the commanded position. The manipulator assembly may move to the commanded position (1052) when the obstacle (1054) is removed. This may happen if the difference between the commanded position and the blocked position remains below the error threshold, thus not causing an updating of the commanded position. However, if the error threshold is exceeded, the commanded position is updated. In this case, the manipulator assembly does not move to the commanded position. Instead, the manipulator assembly may remain at or near the blocked position which now corresponds to the updated commanded position. As a result, when the manipulator arm assembly is under the control of an input control device operated by an operator, the manipulator arm may end up following the commands of the operator with an offset (or with an updated offset, if an offset was already present before hitting the obstacle).

Turning to FIG. 10B2, an additional following task is illustrated. Initially, a commanded state of the manipulator assembly tracks the commanded trajectory (1072). However, only partial completion of the commanded trajectory is possible, due to the presence of an obstacle (1074). More specifically, movement in a y-direction is blocked due to the obstacle, but not in an x-direction. The part of the commanded trajectory that cannot be completed is shown using a dashed line style. When the manipulator assembly comes into contact with the obstacle, the actual y-position no longer follows the commanded y-position on the commanded trajectory. Eventually, the difference between the commanded y-position and the actual y-position exceeds the error threshold, and as a result the commanded y-position is updated. The updated commanded y-position is near the actual y-position. The updated commanded y-position, thus, has a tracking offset as compared to the initially commanded y-position. If a previous tracking offset is already present, the tracking offset may change, as a result of encountering the obstacle. The tracking offset may be maintained as the execution of the following task on the commanded trajectory is continued. Thus, in the example, the commanded state of the manipulator assembly tracks the commanded trajectory with the tracking offset in the y-direction. No tracking offset is introduced in the x-direction. Alternatively, the tracking offset may gradually be reduced as the execution of the following task is continued, and the tracking offset may, thus, be eliminated over time. The tracking offset may be reduced by any function, for example an exponential decay function. The time constant of the exponential decay function may be selected as desired.

Further, the tracking offset may be reduced using a ratcheting feature. The ratcheting feature reduces the tracking offset in a direction-dependent manner. Referring to FIG. 9, when the desired state moves toward the actual state in FIG. 9, the offset used for computing the commanded state may be gradually reduced thereby allowing the commanded state to gradually approach the desired state until the commanded state eventually reaches the desired state. The reduction of the offset may be performed exponentially, linearly, or using any other function, in an offset-dependent manner. The offset may be held constant when the desired state moves away from the actual state. A ratcheting behavior is thus obtained, in which the offset reduces when moving in one direction, while preventing an increase of the offset when moving in the opposite direction.

As an alternative to the following task described in FIG. 10B2, while initially the commanded state may move on the commanded trajectory, once the obstacle is encountered, the commanded state is prevented from progressing on the commanded trajectory. Once the obstacle is removed, the commanded state may resume moving on the commanded trajectory. In this alternative implementation, no tracking offset would be introduced.

Assuming that, for the described following tasks, the commanded trajectory is provided by an operator controlling an input control device, the user may receive a haptic cue when the actual position of the manipulator assembly no longer corresponds to the commanded position on the commanded trajectory. The haptic cue may be, for example, a vibration of the input control device.

While, in the examples, the following tasks are described within the context of an end effector controlled in a Cartesian space, a following task may be performed in a similar manner for single joints.

Embodiments of the disclosure are suitable for various applications. Referring to the manipulator assemblies described in FIGS. 1A, 1B, 2, 3, 4, 5, and 6, the described methods may facilitate and/or improve the use of and interaction with robotic systems. In one embodiment, the methods may cause a manipulator assembly to hold its position or to follow a trajectory unless an error threshold is exceeded. This may allow the manipulator assembly to execute a task, e.g., a telesurgical task. Once the error threshold is exceeded, the manipulator assembly may be allowed to slip, thereby allowing back-driving. Accordingly, if the error threshold is set appropriately, a continuously available slip behavior that does not interfere with task execution is provided. The slip behavior may be advantageous in various situations. Specifically, the slip may reduce the risk associated with collisions of a manipulator assembly with another object. No abrupt movement of the manipulator assembly will occur once an obstacle that blocks movement is removed. The slip may further allow back-driving of the manipulator arm. In addition, the slip may allow a seamless transition from one control mode to another control mode, e.g., when switching a joint from a floating control mode to a position holding control mode. To obtain the desired characteristics, the slip behavior may be customized.

As a first example, the error threshold, whether in a Cartesian space or in a joint space, may be adjusted upward to prevent slip from occurring in the presence of small energy buildups. Similarly, the error threshold may be adjusted downward to allow slip to occur for relatively small energy buildups.

As a second example, error thresholds may be set differently depending on the type of the manipulator assembly (e.g., type of manipulator arm and/or type of tool supported by the manipulator arm). Assume, for example, a scenario that involves multiple manipulator arms. Such a scenario is common in telesurgical applications. One or more manipulator arms may be equipped with a manipulation tool, and another manipulator arm may be equipped with a tool comprising an imaging device, such as an endoscope. In this scenario, different error thresholds for different manipulator arms may be advantageous. It may be desirable to have the manipulator arm with the imaging device be more resistant to slip than any other manipulator arm to ensure that the field of view provided to the surgeon by the imaging device does not change when a collision occurs between one of the tool-carrying manipulator arms and the manipulator arm equipped with the imaging device. Similarly, the use of certain tools involves higher forces than the use of other tools, and the choice of error thresholds may be based at least in the expected forces associated with the tools, and reflect this difference.

As a third example, different joints of the same manipulator assembly may be configured differently to obtain desired characteristics of the associated manipulator arm segments. For some joints, a relatively low error threshold may be selected, whereas for other joints a higher error threshold may be selected. In addition, the slip feature may not be available at all for some joints, for example, for joints that are configured to float. In one example, the slip feature may not be available for the remote center of a manipulator arm. This design choice may ensure that the controller always attempts to keep the remote center in alignment with an aperture through which a tool attached to the manipulator arm passes. The control of the remote center may be performed in Cartesian space. The slip feature may, thus, not be available for joints in joint velocity directions that effect, or could effect, a shift in the remote center. However, the slip feature may be available for one or more joints in joint velocity directions, for example, that allow an end effector or another part of the manipulator assembly to slip without slipping the remote center. Consider, for example, a manipulator assembly with built-in kinematic redundancy (such as the manipulator arm shown in FIG. 5). The redundancy may allow the reconfiguration of some or all of the manipulator arm joints while keeping the tool or the end effector of the tool stationary, or while keeping the remote center stationary. This reconfiguration may be beneficial when an assistant notices an increased risk for a collision of the manipulator arm with an object, e.g., another manipulator arm. The reconfiguration would change the manipulator arm configuration to reduce the collision risk. An on-the-fly reconfiguration may be facilitated by setting a relatively low error threshold in Cartesian space. An assistant may simply push the manipulator arm toward the desired configuration. While the manipulator arm remains under active control to maintain the position of the end effector (or remote center), some of the joints may be allowed to slip in response to the assistant pushing the manipulator arm, thereby completing the reconfiguration movement without disturbing the end effector position and orientation (or the remote center position).

As a fourth example, the slip feature may be implemented for one or more joints of a manipulator assembly, either in Cartesian space or in joint space, to address erroneous or undesired behavior of the manipulator assembly, which may be a result of, for example, a user specifying an improper command via the user control system. Specifically, an assistant in proximity to the manipulator assembly may prevent such behavior by manually blocking the erroneous or undesired movement. The controller may be configured to stop executing the erroneous or undesired movement when the movement is blocked for at least a specified time interval. If the blockage is brief (i.e., for less than the specified time interval, which may occur to due accidental interference of the assistant with the movement of the manipulator assembly), the controller may be configured to continue executing the movement. In contrast, when the blockage continues for at least the specified time interval, the controller may be configured to abandon the movement, such as by halting the execution of the movement while the movement is partially executed.

While the invention has been described with respect to a limited number of embodiments, those skilled in the art, having benefit of this disclosure, will appreciate that other embodiments may be devised which do not depart from the scope of the invention as disclosed herein. Accordingly, the scope of the invention should be limited only by the attached claims.

What is claimed is:

1. A computer-assisted medical system comprising:
- a manipulator arm; and
- a controller comprising a computer processor, the controller configured with at least a non-clutch mode,
- wherein when in the non-clutch mode, the controller is configured to servo, by a feedback controller comprising a proportional control gain, at least one joint associated with at least one manipulator arm segment of the manipulator arm, the servoing comprising executing a servo loop comprising:
  - obtaining an actual state of the manipulator arm,
  - computing a difference between a commanded state and the actual state, the commanded state used for the servoing the at least one joint,
  - determining whether the difference exceeds an error threshold,
  - based on determining that the difference does exceed the error threshold:
    - updating the commanded state using an offset to reduce the difference,
    - wherein the updating the commanded state reduces an energy buildup in the servo loop, the energy buildup associated with the proportional control gain operating on the difference between the commanded state and the actual state, and
    - applying the commanded state to control the actual state, and
  - based on determining that the difference does not exceed the error threshold:
    - not updating the commanded state, and
    - applying the commanded state to control the actual state.

2. The computer-assisted medical system of claim 1, wherein the commanded state and the actual state each comprises a joint state.

3. The computer-assisted medical system of claim 1, wherein the commanded state and the actual state each comprises: an end effector position, an end effector orientation, an end effector velocity, or an end effector force.

4. The computer-assisted medical system of claim 1, wherein the at least one joint comprises a first joint and a second joint, wherein the determining whether the difference exceeds the error threshold is performed separately for the first and the second joints, wherein the error threshold comprises a first error threshold for the first joint and a second error threshold for the second joint, and wherein the first error threshold is different from the second error threshold.

5. The computer-assisted medical system of claim 1, wherein the error threshold is selected based on at least one characteristic selected from the group consisting of: a type of tool supported by the manipulator arm and a desired characteristic of the at least one manipulator segment.

6. The computer-assisted medical system of claim 1, wherein the non-clutch mode is a mode used to perform at least one task selected from the group consisting of: a position holding task, a following task, and a positioning task.

7. The computer-assisted medical system of claim 6, wherein the non-clutch mode is the mode used to perform the position holding or following task, and wherein when performing the position holding task or following task, updating the commanded state comprises setting the commanded state in close proximity to the actual state.

8. The computer-assisted medical system of claim 7, wherein the non-clutch mode is reached by switching from another mode, and wherein the setting the commanded state in close proximity to the actual state dissipates an excessive energy buildup in the servo loop when a discrepancy between the commanded state and the actual state is present during the switching.

9. The computer-assisted medical system of claim 6, wherein the positioning task is performed using a position time (PT) interpolation or a position velocity time (PVT) interpolation.

10. The computer-assisted medical system of claim 1, wherein the commanded state is governed by a desired state obtained from an input control device under the control of an operator, adjusted by the offset.

11. The computer-assisted medical system of claim 1, wherein when in the non-clutch mode, the controller is further configured to:

gradually reduce the offset over time, and update the commanded state using the gradually reduced offset, over time.

12. The computer-assisted medical system of claim 1, wherein the commanded state and the actual state each comprises a state in a Cartesian reference frame.

13. A method for operating a medical system, comprising:

in a non-clutch mode, servoing, by a feedback controller comprising a proportional control gain, at least one joint associated with at least one manipulator arm segment of a manipulator arm of the medical system, the servoing comprising executing a servo loop comprising:

obtaining an actual state of the manipulator arm;

computing a difference between a commanded state and the actual state, the commanded state used for servoing the at least one joint;

determining whether the difference exceeds an error threshold;

based on determining that the difference does exceed the error threshold:

updating the commanded state using an offset to reduce the difference, wherein the updating the commanded state reduces an energy buildup in the servo loop, the energy buildup associated with the proportional control gain operating on the difference between the commanded state and the actual state, and applying the commanded state to control the actual state; and based on determining that the difference does not exceed the error threshold:

not updating the commanded state, and applying the commanded state to control the actual state.

14. The method of claim 13, wherein the at least one joint comprises a first joint and a second joint, wherein the determining whether the difference exceeds the error threshold is performed separately for the first and second joints, wherein the error threshold comprises a first error threshold for the first joint and a second error threshold for the second joint, and wherein the first error threshold is different from the second error threshold.

15. The method of claim 13, wherein the error threshold is selected based on at least one characteristic selected from the group consisting of: a type of tool supported by the manipulator arm and a desired characteristic of the at least one manipulator segment.

16. The method of claim 13, wherein the non-clutch mode is a mode used to perform a position holding or following task, and wherein updating commanded state comprises setting the commanded state in close proximity to the actual state.

17. The method of claim 13, further comprising:

obtaining a desired state from an input device under the control of an operator, wherein the commanded state is governed by the desired state, adjusted by the offset.

18. The method of claim 13, further comprising, in the non-clutch mode:

gradually reducing the offset over time; and updating the commanded state using the gradually reduced offset, over time.

* * * * *